(12) United States Patent
Kramer et al.

(10) Patent No.: US 9,810,626 B2
(45) Date of Patent: Nov. 7, 2017

(54) OPTOELECTRONIC SENSOR AND METHOD FOR THE TRANSMISSION MONITORING OF A FRONT SCREEN

(71) Applicant: SICK AG, Waldkirch (DE)

(72) Inventors: Joachim Kramer, Waldkirch (DE);
Michael Engler, Waldkirch (DE);
Markus Hammes, Waldkirch (DE);
Christof J. Meyer, Waldkirch (DE)

(73) Assignee: SICK AG, Waldkirch (DE)

( * ) Notice: Subject to any disclaimer, the term of this patent is extended or adjusted under 35 U.S.C. 154(b) by 35 days.

(21) Appl. No.: 15/092,991

(22) Filed: Apr. 7, 2016

(65) Prior Publication Data

US 2016/0299072 A1 Oct. 13, 2016

(30) Foreign Application Priority Data

Apr. 8, 2015 (DE) .................. 10 2015 105 264

(51) Int. Cl.
*G01N 21/59* (2006.01)
*G01S 17/42* (2006.01)
(Continued)

(52) U.S. Cl.
CPC ............. *G01N 21/59* (2013.01); *G01D 5/30* (2013.01); *G01M 11/00* (2013.01); *G01S 7/4817* (2013.01);
(Continued)

(58) Field of Classification Search
CPC ...................................................... G01N 21/59
(Continued)

(56) References Cited

U.S. PATENT DOCUMENTS

| | | | |
|---|---|---|---|
| 7,030,968 B2* | 4/2006 | D'Aligny | G01B 11/002 356/139.1 |
| 8,692,983 B1* | 4/2014 | Chapman | G01P 5/26 342/124 |
| 2008/0158555 A1 | 7/2008 | Mori | |

FOREIGN PATENT DOCUMENTS

| | | |
|---|---|---|
| DE | 43 45 446 C2 | 6/1994 |
| DE | 9321155 U1 | 6/1996 |

(Continued)

OTHER PUBLICATIONS

Office Action dated Feb. 22, 2016 issued in corresponding German Application No. 10 2015 105 264.4.

*Primary Examiner* — Tarifur Chowdhury
*Assistant Examiner* — Omar Nixon
(74) *Attorney, Agent, or Firm* — Nath, Goldberg & Meyer; Jerald L. Meyer (57) ABSTRACT

An optoelectronic sensor (10) for detecting objects in a monitored zone (20) is provided which has the following: a front screen (38); a light transmitter (12) for transmitting a light beam (16); a movable deflection unit (18) for the periodic sampling of the monitored zone (20) by the light beam (16); a light receiver (26) for generating a received signal from the light beam (22) remitted by the objects; at least one test light transmitter (42); at least one test light transmitter (42), at least one test light receiver (44) and at least one test light reflector (48) which span a test light path (46*a-b*) through the front screen (38); and an evaluation unit (32) which is configured to acquire pieces of information on the objects in the monitored zone (20) from the received signal and to recognize an impaired light permeability of the front screen (38) from a test light signal which the test light receiver (44) generates from test light which is transmitted from the test light transmitter (42) and which is reflected at the test light reflector (48). In this respect, the test light
(Continued)

reflector (48) is arranged such that it moves along with the deflection unit (18).

14 Claims, 3 Drawing Sheets (51) Int. Cl.
*G01S 7/481* (2006.01)
*G01S 7/497* (2006.01)
*G01D 5/30* (2006.01)
*G01M 11/00* (2006.01)

(52) U.S. Cl.
CPC .............. *G01S 7/497* (2013.01); *G01S 17/42* (2013.01); *G01N 2201/06113* (2013.01); *G01N 2201/1053* (2013.01); *G01S 2007/4975* (2013.01)

(58) Field of Classification Search
USPC ......................................................... 356/432
See application file for complete search history.

(56) References Cited

FOREIGN PATENT DOCUMENTS

| DE | 202009004397 U1 | 8/2010 |
|----|-----------------|--------|
| EP | 0924535 A2 | 6/1999 |
| EP | 2 237 065 A1 | 6/2010 |
| EP | 2447733 A1 | 5/2012 |
| EP | 2482094 A1 | 8/2012 |
| EP | 2 508 914 A1 | 10/2012 |
| WO | 2007/031359 A1 | 3/2007 |

\* cited by examiner

OPTOELECTRONIC SENSOR AND METHOD FOR THE TRANSMISSION MONITORING OF A FRONT SCREEN

The invention relates to an optoelectronic sensor and to a method for the transmission monitoring of a front screen of an optoelectronic sensor in accordance with the preamble of claim 1 or claim 13 respectively.

Laser scanners are frequently used for visual monitoring. In this respect, a light beam generated by a laser periodically scans a monitored zone with the aid of a deflection unit. The light is remitted at objects in the monitored zone and is evaluated in the scanner. A conclusion is drawn on the angular location of the object from the angular position of the deflection unit and additionally on the distance of the object from the laser scanner from the light transit time while using the speed of light. In this respect, two general principles are known to determine the light transit time. In phase-based processes, the transmitted light is modulated and the phase shift of the received light with respect to the transmitted light is evaluated. In pulse-based processes, as they are preferably used in safety engineering, the laser scanner measures the transit time until a transmitted light pulse is received again.

An important application is the securing of a danger source in safety engineering. The laser scanner in this respect monitors a protected field which may not be entered by operating personnel during the operation of the machine. Since the laser scanner acquires angle and distance information, two-dimensional positions of objects in the monitored zone and thus also in the protected field can be determined. If the laser scanner recognizes an unallowed intrusion into the protected field, for instance a leg of an operator, it triggers an emergency stop of the machine.

Sensors used in safety engineering have to work particularly reliably and must therefore satisfy high safety requirements, for example the EN13849 standard for safety of machinery and the machinery standard EN61496 for electrosensitive protective equipment (ESPE). A number of measures have to be taken to satisfy these safety standards such as reliable electronic evaluation by redundant, diverse electronics, function monitoring and/or provision of individual test targets with defined degrees of reflection which have to be recognized at the corresponding scanning angles.

A further one of these safety requirements is the recognition of an impairment of the transmission of a front screen of the laser scanner which on a restriction of the detection capability must be responded to by way of a safety-directed shutdown. In this respect, both a homogeneous contamination, for instance through dust, and a selective impairment by small interference objects are to be revealed from a defined minimum size. A deliberate manipulation by covering front screen regions using small shading objects likewise has to be excluded.

To reveal such interference influences, a laser scanner typically uses optical test channels which check different positions of the front screen region by means of irradiation. In a solution known by way of example from DE 43 45 446 C2, a plurality of independent optical test channels are distributed over the total angular range of the front screen and correspondingly irradiate different regions of the front screen by way of a test and thereby recognize an impaired transmission. The distribution of the test channels has to be dense enough in order to securely detect the small contamination objects or manipulation objects which are required by the standard and indeed detect them everywhere, despite only selective detection. A large number of test channels naturally increases the manufacturing costs and the required construction space. Furthermore, the test channels lie very close to the outer contour of the laser scanner in order to evade the rotating deflection unit. They thus become prone to interferences by extraneous light and by reflectors which are located in the vicinity at random or for manipulation. In order to obtain defined test regions, the optoelectronic components have to be partially shaded by diaphragms in a manner demanding in effort and cost.

Having regard to laser scanners having a biaxial design, that is having a transmitted light beam and a received light beam which extend next to one another, an additional problem results with small shading objects on the front screen, with the problem originally not affecting the transmission capability of said small shading objects, but conventionally also being revealed by the front screen monitoring. The reception lens of a laser scanner is typically a multizone lens having a close range zone in the center in order to receive at least more or less constant levels independently of the object distance, that is to achieve signal dynamics which are as constant as possible. On a covering of this close range zone by a shading object on the front screen, the laser scanner thus suffers a large loss of its detection capability in the proximal range. Such a manipulation immediately stands out in coaxial systems since the transmitted beam is also blocked and, for example, makes itself noticeable through strong scattered light. In a biaxial system, in contrast, the transmitted light beam does not extend through the close range zone. It is possible to give the front screen monitoring the additional function of revealing such shading objects. However, test channels which lie particularly close together have to be used for this purpose.

EP 2 237 065 A1 discloses a laser scanner in which the complete measurement unit including the light source and the detector rotates. A test light source and a test detector are furthermore accommodated on the corresponding rotor, whereas a reflector element is arranged outside the housing. The test light source and the test detector thus sample the front screen in the course of the rotation with the aid of the reflector element. However, such systems having a rotating measurement head have the disadvantage that a data connection and an energy supply have to be provided between the stationary part and the rotating measurement head. Furthermore, the test light detector is inevitably directed outwardly and can therefore be disturbed relatively easily by extraneous light.

It is therefore the object of the invention to improve the front screen monitoring.

This object is satisfied by an optoelectronic sensor and by a method for the transmission monitoring of a front screen of an optoelectronic sensor in accordance with claim 1 or claim 12 respectively. A test light transmitter, a test light receiver and a test light reflector span a test channel or a test light path in order to check the light permeability of the front screen. In this respect, the invention starts from the basic idea of monitoring the transmission using a test channel not only in a selective manner, but rather over a larger region of the front screen. For this purpose, the test light reflector is moved along with the deflection unit. If the deflection unit is a rotating mirror as is frequently the case, the test light reflector is preferably attached thereto and thus co-executes the rotary movement.

The invention has the advantage that a spatially resolved transmission measurement is made possible using simple means and recognizes a loss which can no longer be tolerated, for example due to contamination or shading objects, and thus ensures the detection capability. Significantly fewer test light paths are required for this purpose due to the test light reflector which moves along and the system becomes less complex, less expensive and smaller. An increased robustness with respect to interferences by extraneous light and by reflectors is furthermore achieved by an inwardly disposed optical path on the test light path and by an inwardly directed receiver axis. More freedom arises with respect to the positions monitored at the front screen. A mechanical component for shading and for passage separation can be dispensed with by a small surface of the test light reflector.

The test light transmitter and the test light receiver are preferably not arranged such that they move along with the deflection unit. The test light transmitter and the test light receiver are thus located in the resting part of the sensor, for instance, in a base or in a housing in which the movable deflection unit is installed. This significantly reduces the complexity of the system, since no supply and no data exchange for a movable or rotating system have to be provided. On the other hand, a few of the sensors already provide a movable measurement head for the light transmitter and for the light receiver as a deflection unit. In principle, the problem of the connection is thus manageable and such a connection can therefore also be added for the transmission monitoring or can even also additionally be used within a sensor having a movable measurement head without substantial additional effort. Consequently, it is by all means conceivable to allow the test light transmitter and the test light receiver to move along as well, for example via a type of balcony which is attached to the movable deflection unit in order to hold the test light transmitter and the test light receiver or alternatively, in reversal of the light path, the test light reflector such that they move along.

A plurality of test light transmitters and test light receivers are preferably arranged distributed around the deflection unit in a peripheral direction. In this respect, a test light transmitter and a test light receiver even more preferably respectively form a pair and a plurality of such pairs are distributed over the periphery in order to monitor a peripheral front screen in a plurality of regions in a spatially resolved manner. Since the test light reflector is moved along, a single test light reflector is sufficient in order to form corresponding test channels with the plurality of pairs. Different positions on the front screen can be sampled by a control in time of the test channels during the operation. It is naturally nevertheless conceivable to attach a plurality of test light reflectors at different angles to the deflection unit.

The evaluation unit is preferably configured to acquire a piece of information on the position of the deflection unit from the test light signal. The test paths are bound to the deflection unit via the test light reflector which moves along. It is therefore also possible to acquire at least approximate pieces of information on the respective position, in particular on the angular position of the deflection unit, from the identity of the respective active test channel and possibly also from an expected intensity of the test light which is dependent on the position of the deflection unit. An otherwise typical encoder for the detection of the angular position of the deflection unit can thus be supplemented or even replaced. A diversely redundant second source for pieces of information on the angular positions at least results and can particularly be used in safety engineering for a check of the encoder and for a plausibility test of the encoder.

The test light reflector preferably has retroreflecting properties. For this purpose, the test light reflector can be a retroreflector, for example, having structures similar to a Catseye (reflector stud). Alternatively, the test light reflector has one or more convex or concave mirror surfaces or a plurality of planar mirror surfaces which are at an angle with respect to one another and which reflect at least some of the incident test light in the direction of incidence. The reflection behavior of such a mirror, not only a retroreflector in the narrower sense, is here considered as a retroreflecting property. The retroreflecting properties bring about that the test light returns to the test light receiver over a total angular range during the movement of the test light reflector and forms a test light path in this manner. The front screen can thus be checked for transmission over a corresponding angular range and significantly fewer test channels are sufficient in order to cover the front screen. Without retroreflecting properties, for example as a simple mirror surface, the front screen can only be tested in a smaller range by the test light reflector since a complete test light path is only formed in a restricted angular range. However, more than only a selective range is also tested by the finite extent of the mirror surface such that a simple mirror surface also already brings substantial advantages with respect to a conventional static test path. On a use of a retroreflector, the test light transmitter and the test light receiver have to lie very close to one another. In contrast, with a planar mirror there is the freedom of placing the test light receiver at a different position than the test light transmitter.

The test light reflector preferably has a plurality of part reflectors which are arranged above one another and/or which are tilted with respect to one another. The test light path is widened by such staggered part reflectors and in particular allows a plurality of samplings of the front screen at different vertical positions. A simple test light receiver can only evaluate the sum of this plurality of samplings, but it can at least reveal an impairment of the transmission. The vertical position at which the transmission is varied is also recognized by a spatially resolving test light receiver.

The front screen preferably has the shape of a rotational body and has an inwardly facing contour in a section thereof with respect to a central axis of the rotational body, wherein the test light transmitter and the test light receiver are arranged in a region of the front screen where said front screen has a small radius. A truncated cone or a spherical section is an example of this shape of the front screen. In this respect, the front screen allows a clearance with respect to a corresponding cylinder by means of the inwardly facing contour, with the test light transmitter and the test light receiver being able to be arranged in said clearance. Since the test light reflector is located at the deflection unit, a test light path arises that is disposed very far inwardly hardly, that is hardly disturbed by extraneous light and that is correspondingly robust.

The front screen preferably has a peripheral base. The radius of the inwardly facing contour is thus quickly returned outwardly again. The test light receiver and the test light transmitter can be accommodated beneath this base and are thus also disposed in the interior of the sensor in a protected manner. The test light path then first passes through the base into the free space and subsequently passes through the actual front screen up to the test light reflector for the actual transmission test.

The light transmitter and the light receiver of the optical distance measurement system are preferably arranged next to one another in a biaxial design with mutually parallel optical axes. In contrast to this, a coaxial design is conventionally frequently selected instead in which the smaller cross-section of the transmitted beam is disposed centrally in the received beam. However, a biaxial arrangement is actually simpler having regard to a small manner of construction.

A reception lens is preferably arranged upstream of the light receiver and has a close range zone which is significantly larger than a masking by a normed cover object. As explained in the introduction, the close range zone serves to adapt the signal dynamics in the proximal range in a desired manner. It is conventionally possible to mask the proximal range using small objects and a transmission measurement of the front screen which is correspondingly demanding in effort in cost therefore has to be carried out using very many test channels. An enlarged close range zone is insensitive to this interference or manipulation by small objects since it can no longer be masked as easily. Accordingly, significantly fewer test channels are sufficient for the transmission measurement and the detection reliability is increased. The provision of a plurality of close range zones which are separate from one another or which are distributed or, for example, a ring-like close range zone in particular at the outer margin of the reception lens are examples of enlarged close range zones.

The sensor is preferably configured as a safety light scanner, wherein the evaluation unit is configured to compare the position of detected objects with protected fields and to control a safe output using a shut-down signal on recognizing an unallowed intrusion into a protected field. The simplified front screen monitoring is in particular of advantage for such applications.

The method in accordance with the invention can be further developed in a similar manner and shows similar advantages in this respect. Such advantageous features are described in an exemplary, but not exclusive manner in the dependent claims following the independent claims.

The invention will be explained in more detail in the following also with respect to further features and advantages by way of example with reference to embodiments and by means of the enclosed drawing. The Figures of the drawing show in.

Figure 1:
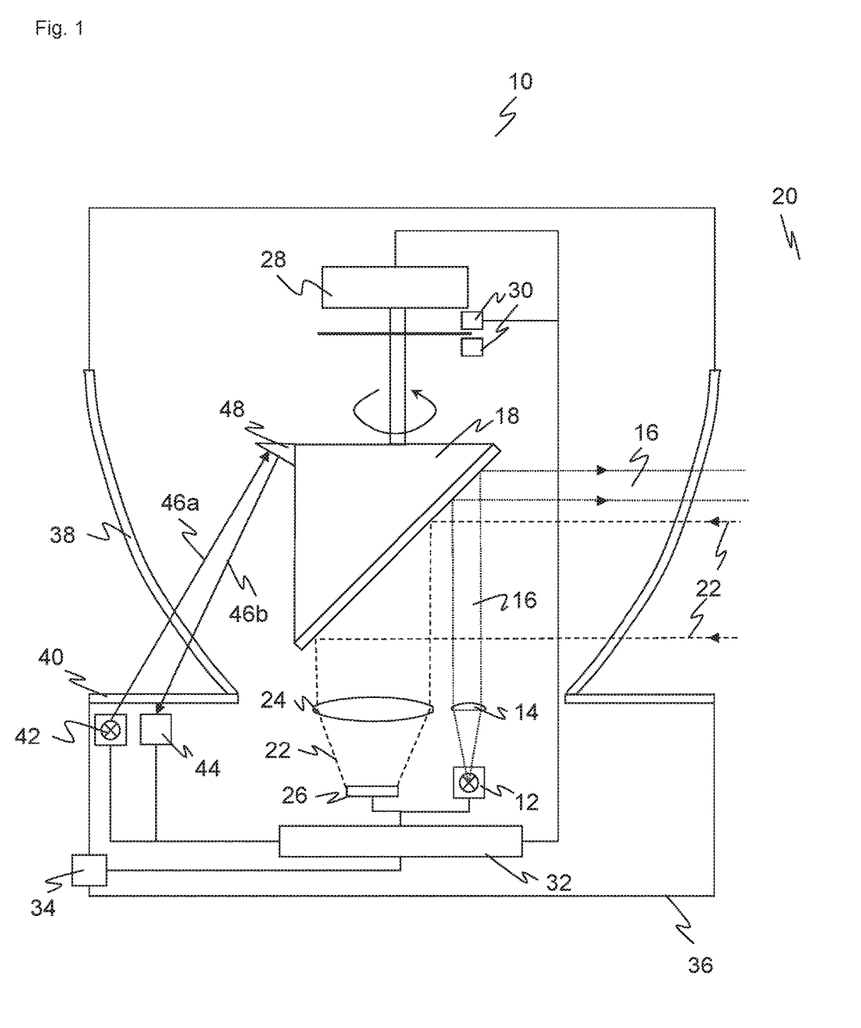
FIG. 1 a sectional representation of an embodiment of a laser scanner.

FIG. 1 shows a schematic sectional representation through a laser scanner 10 in accordance with the invention which is in particular configured as a distance-measuring safety laser scanner. A light transmitter 12, for instance a laser in the form of an edge emitter or of a VCSEL, transmits a light signal, for example, in the form of brief light pulses or of periodically amplitude-modulated light. The transmitted light is collimated by a transmission optics 14 into a transmitted light beam 16 which is deflected via a movable deflection unit 18 into a monitored zone 20 and is there remitted or reflected by an optionally present object. Some of this light returns to the laser scanner 10 as an incident remitted light beam 22 and is deflected by the deflection unit 18 to a reception optics 24 and is bundled from there onto a light receiver 26, for example, a photodiode or an APD (Avalanche Photo Diode).

The deflection unit 18 can be configured as a pivot mirror, but is generally a rotating mirror which rotates continuously by the drive of a motor 28. The respective angular position of the deflection unit 18 is detected via an encoder 30. The light beam 16 generated by the light transmitter 12 thus scans the monitored zone 20 generated by the movement. If a remitted light beam 22 from the monitored zone 20 is received by the light receiver 26, a conclusion can be drawn on the angular location of the object in the monitored zone 20 from the angular position of the deflection unit 18 by means of the encoder 30.

In addition, the light transit time from the transmission of the light beam 16 up to the reception of the remitted light beam 22 after reflection at the object in the monitored zone 20 is determined. All light transit time processes are conceivable for this purpose. A conclusion is drawn on the distance of the object from the laser scanner 10 from the light transit time while using the speed of light. This evaluation takes place in an evaluation unit 32 which is connected to the light transmitter 12, to the light receiver 26, to the motor 28 and to the encoder 30 for this purpose.

Two-dimensional polar coordinates of all the objects in the monitored zone 20 are then available via the angle and via the distance. Two-dimensional protected fields into which unallowed objects such as operating personnel or their body parts may not reach can thus be defined in the monitored zone 20. If the evaluation unit 32 recognizes an unallowed intrusion into a protected field, a safety-directed shut-down signal is output via a safe output 34 (OSSD, Output Signal Switching Device) in order, for example, to stop a monitored dangerous machine or to move it into a non-dangerous position. Alternatively, measured data are output via the output 34, above all when the laser scanner 10 is not a safety laser scanner and accordingly does not monitor any protected fields.

All the mentioned functional components are arranged in a housing 36 which has a peripheral front screen 38 in the region of the light exit and of the light entry. The front screen 38 is frequently, but not inevitably, configured as a rotational body and in both cases also does not necessarily have to extend over 360° such that a certain angular range then remains as a dead zone.

The front screen 38 has an inwardly directed contour which is curved in the shape of a cup in the example of FIG. 1. However, a different curvature and even a straight contour are also conceivable, which then overall results in the shape of a truncated cone. In the lower region, the front screen 38 is terminated by a base 40 which again returns the radius which is reduced above due to the inwardly directed contour.

A test light transmitter 42 and a test light receiver 44 are arranged beneath this base 40. The test light transmitter 42 is any desired light source whose spectrum preferably differs from the light transmitter 12 to avoid scattered light, but tests the front screen 38 for transmission in a relevant wavelength range. The test light receiver can be a simple photodiode, wherein a spatial resolution is of advantage in a few embodiments. Further pairs of test light transmitters and test light receivers are preferably distributed around the periphery of the front screen 38, but are not shown in FIG. 1. The test light of the test light transmitter 42 first passes through the base 40 on a test light path 46a-b into the free space and then radiates through the front screen 38 into the interior of the laser scanner 10. There it is reflected at a test light reflector 48 which is attached to the deflection unit 18 and returns to the test light receiver 44 for the completion of the test light path 46a-b on a renewed irradiation of the front screen 38 and of the base 40. Alternatively, the test light receiver 44 is inwardly disposed such that the front screen 38 is only irradiated once. With reference to the test signal of the test light receiver 44, the evaluation unit 32 can, for example by comparison with a desired level, check whether the light permeability of the front screen 38 is impaired at the piercing points of the test light path 46*a-b*. A test for homogeneous contamination or for the presence of shading objects on the front screen 38 thereby becomes possible. A safety-directed shutdown is triggered in a safety laser scanner on recognizing an impairment which no longer ensures its reliable function. A sensor which is not used in safety engineering could instead also indicate only a maintenance demand, for example.

The test light reflector 48 co-executes the rotary movement of the deflection unit 18. The test light path 46*a-b* is thereby also dynamic since one of the and points moves with the test light reflector 48. As will be explained in more detail in the following with reference to FIGS. 2 to 4, the front screen 38 can thus be monitored for its transmission properties not only selectively, but rather over a total range in the course of the rotary movement. The evaluation unit 32 naturally has to take into account the rotary movement on controlling the test channels formed by the test light transmitters 42 and by the test light receivers 44 via the test light reflector 48. Conversely, however, the test channels can also be used to acquire apiece of information on the angular position of the deflection unit 18. An approximate piece of angular information is already included in the position of that pair of test light transmitter 42 and test light receiver 44 which can in each case currently generate a test light signal via the test light reflector 48. However, the intensity and the point of incidence of the test light on the test light receiver 44 can also vary with the respective position of the test light reflector 48 in dependence on the arrangement of the test light path 46*a-b* and on the properties of the test light reflector 48. A more precise piece of angular information can thereby also be detected by means of which the measurement information of the encoder 30 can, for example, be checked for plausibility or the encoder 30 can even be replaced.

The laser scanner 10 in accordance with FIG. 1 has a biaxial arrangement in which the transmitted light beam 16 extends next to the incident remitted light beam 22. However, this should only be understood by way of example. A transmission check of the front screen 38 via a test light reflector 48 which moves along is also possible in every other design of a corresponding optoelectronic sensor having a deflection unit which is moved periodically.

Figure 2:
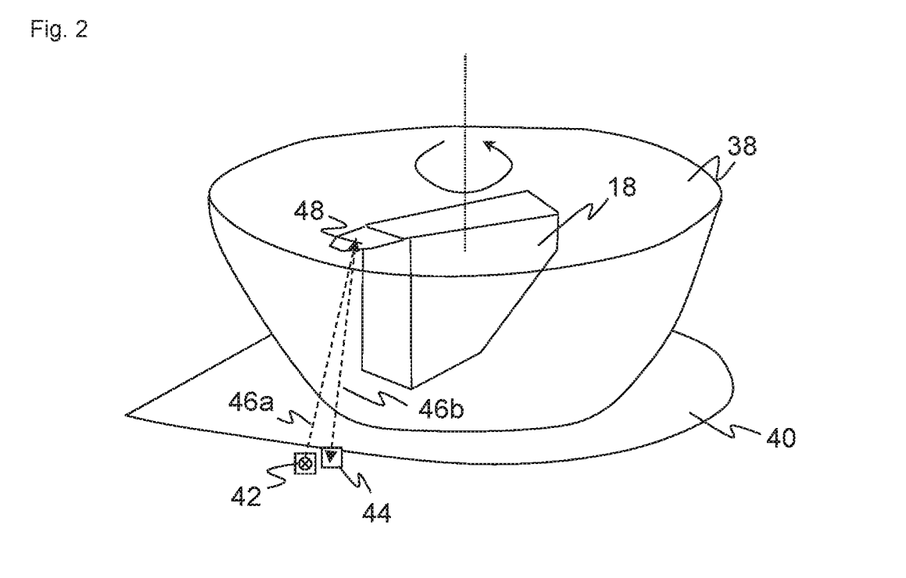
FIG. 2 a three-dimensional representation of a front screen of a laser scanner, for illustrating a test light path.

FIG. 2 shows a further three-dimensional view of the front screen 38 having a base 40 and of the deflection unit 18 with the test light reflector 48 which moves along. For better clarity, only one test channel having a pair of test light transmitter 42 and test light receiver 44 is shown again.

Figure 3:
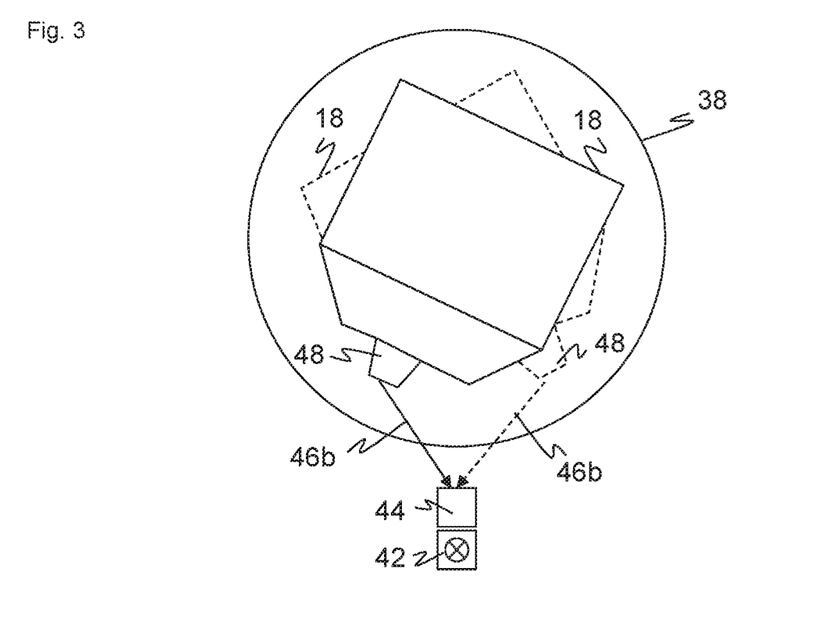
FIG. 3 a schematic plan view of a deflection unit of a laser scanner at two different angular positions with associated test light paths.

FIG. 3 is a supplementary associated plan view at two exemplary angular positions of the deflection unit 18, and thus also of the test light reflector 48, which are each shown by broken lines, i.e. by dashed lines.

The test light path 46*a-b* is transposed by the rotation of the deflection unit 18 and the piercing point through the front screen 38 migrates over an extended region. The transmission check therefore takes place in the same test channel not only at a fixed azimuth angle, but rather over an entire azimuth angular range. A smaller number of test channels having a respective static pair of test light transmitter 42 and test light receiver 44 is thereby sufficient in order to check the front screen 38 for all relevant azimuth angles.

The test light reflector 48 preferably has retroreflecting properties. As can be recognized from FIG. 3, the test light is thereby again reflected to the test light receiver 44 at different azimuth angles. The test light reflector 48 is for this purpose preferably configured as a retroreflector or as an arrangement of a plurality of retroreflectors. Alternatively, a contoured mirror can be used which at least partly reflects light from different angles of incidence by way of its inclination or by multiple reflections. A transmission check is also possible using a simple mirror surface as a test light reflector 48. In this respect, there is more freedom in the arrangement of test light transmitter 42 and test light receiver 44; only a smaller range of the front screen 38 is tested for this purpose.

Figure 4:
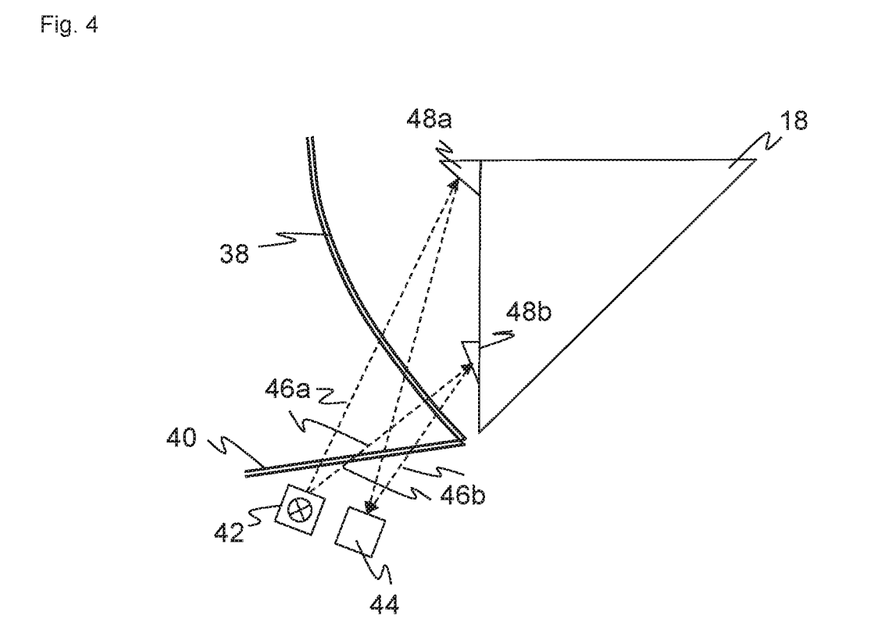
FIG. 4 a schematic sectional representation of a detail of a front screen of a laser scanner with test light paths at a divided test light reflector for the front screen monitoring at a plurality of vertical positions.

FIG. 4 shows a simplified sectional representation of the front screen 38 and of a test channel in a further embodiment. In this respect, the test light reflector 48 has two or more part reflectors 48*a-b* which are arranged above one another and/or which are tilted with respect to one another. Whereas the moving along of the test light reflector 48 ensures a sampling of the front screen 38 over an azimuth angular range, the part reflectors 48*a-b* also allow a sampling via different polar angles or vertical regions. It is usually sufficient to generate only one summed total signal of all the part reflectors 48*a-b* in the test light receiver 44 since a safety-critical impairment is thus already recognized. However, if a contamination or a shading object should be localized, the test light receiver 44 can thus also be configured in a spatially resolving manner.

The required number of test channels can already be significantly reduced by the moving along of the test light reflector 48. As explained in the introduction, it must additionally be ensured with a biaxial design of the laser scanner 10 as in FIG. 1 that shading object does not mask the proximity zone of the reception optics 24.

Figure 5:
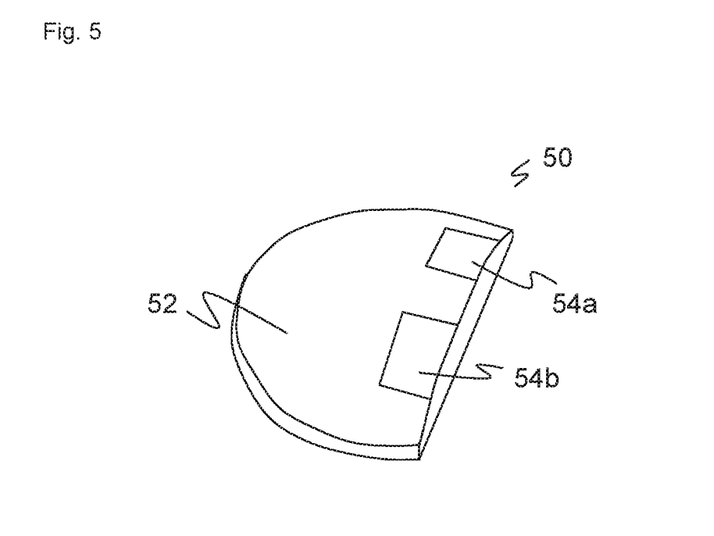
FIG. 5 a three-dimensional view of a reception lens with an extended proximity zone.

FIG. 5 shows a reception lens 50 which can be used in the reception optics 24 or as the reception optics 24 and in which the signal of objects in the proximal range can no longer be masked completely by individual small shading objects. The resistance to manipulation thereby increases and it is no longer required that the transmission monitoring takes over this function of the manipulation recognition. This allows a further reduction in the number of required test channels.

The lens 50 has a main part 52 which is configured as convex or plano-convex. Overall, it is therefore a converging lens for bundling the remitted light beam 22. The lens is cut off at the right hand side in FIG. 5 in order to move the transmission path and the reception path closer to one another. This cutting off is not absolutely necessary.

The lens 50 furthermore has an extended proximity zone 54*a-b* which is divided into two here. A proximity zone per se is known and, as described in the introduction, serves to elevate the signal dynamics for short distances by other bundling properties than the main part 52. It is additionally achieved by the spatial separation into two or more proximity zones 54*a-b* that the signal in the proximal range can no longer be masked completely by individual small objects. An improved robustness with respect to selective contaminations and manipulations is therefore achieved in this manner up to a defined maximum size of the interference object or of the manipulation object.

A divided proximity zone 54*a-b* is only one example for a distribution of the proximity zone onto a larger region. The described advantage can also be achieved if the proximity zone extends in a different manner onto a region which cannot be masked by small objects. A further example is therefore a ring-like proximity zone in the vicinity of the outer margin of the reception lens 50.

The previously described embodiments relate to a test light reflector 48 which moves along or which rotates along and to static test light transmitters 42 or test light receivers 44. It is also conceivable to accommodate the test light transmitter 42 and the test light receiver 44 on a type of balcony of the deflection unit 18 and thus likewise to rotate them along. A single pair of test light transmitter 42 and test light receiver 44 is then sufficient in order to sample the front screen 38 in the course of the rotary movement at all azimuth angles.

These embodiments of a transmission measurement using a test light reflector 48 which moves along should finally be used as a basis for systematically listing how test channels can be designed with static elements or with elements which move along.

In a first family, test light paths are formed reflectively from a test light transmitter, test light reflector and test light receiver. Each of these elements can be static or can move along so that eight combinations result overall. In four of these combinations, the test light transmitter moves with respect to the test light receiver. This is not a sensible configuration for a reflective test light path. The test light transmitter and the test light receiver should much rather either both be static or both move along such that they always lie statically to one another and frequently lie next to one another. In two of the remaining combinations, the test light reflector moves with the deflection unit. If the test light transmitter and the test light receiver are static, this corresponds to the embodiments explained in detail above with reference to the Figures. On a moving along of the test light transmitter and of the test light receiver, the embodiment arises which is likewise described above subsequent to the description of the Figures. The test light reflector is static in the remaining two combinations. With a likewise static test light transmitter and test light receiver, this than corresponds to the procedure in accordance with DE 43 45 446 C2 mentioned in the introduction and with the test light transmitter and test light receiver which move along, this corresponds to the procedure in accordance with EP 2 237 065 A1 mentioned in the introduction.

In a second family, test light paths are formed directly, that is without a test light reflector. The pair of test light transmitter and test light receiver is in this respect directly facing one another through the front screen and one element is located on the inside and one on the outside with respect to the front screen. On a configuration of the front screen having a base, the test light transmitter and the test light receiver can both be inwardly disposed by a two-times piercing through of the front screen, wherein one element is then arranged beneath the base. Leaving both elements static in this respect is a known and operable solution which, however, requires a corresponding plurality of test channels. It is possible to leave the outwardly disposed element static and to move the inwardly disposed element by the deflection unit, but an element which moves along has to be controlled and provided for this purpose. Furthermore, the test light transmitter should preferably be moved along since the test light receiver otherwise looks outward and thus also detects extraneous light. The deflection unit could in principle also have a type of balcony which reaches beneath the base of the front screen. In this manner, the test light transmitter and the test light receiver can be moved along and a single test channel is sufficient. However, this balcony represents a major mechanical challenge in order to avoid disadvantageous effects on the deflection unit by an imbalance.

In a third family, test light paths are formed by the actual scanning beam of the light transmitter 12. The light transmitter 12 therefore simultaneously acts as a test light transmitter. In principle, all the variants mentioned in the previous paragraphs are possible with this replacement, but there is a respective large risk of cross-talk into the actual measurement passage since a small portion of the measurement beam would have to be branched off in this case and would have to be directed onto the test light receiver after a single or multiple irradiation of the front screen. There is thereby no longer a possibility of directly suppressing this optical echo from the proximal range which is extremely harmful to the measurement system.

The invention claimed is:

1. An optoelectronic sensor for detecting objects in a monitored zone, said optoelectronic sensor having the following:
a front screen;
a light transmitter for transmitting a light beam;
a movable deflection unit for a periodic sampling of the monitored zone by the light beam;
a light receiver for generating a received signal from the light beam remitted by the objects;
at least one test light transmitter, at least one test light receiver and at least one test light reflector which span a test light path through the front screen;
and an evaluation unit which is configured to acquire pieces of information on the objects present in the monitored zone from the received signal and to recognize an impaired light permeability of the front screen from a test light signal which the test light receiver generates from test light which is transmitted from the test light transmitter and which is reflected at the test light reflector,
wherein the test light reflector is arranged such that it moves along with the deflection unit.

2. The optoelectronic sensor in accordance with claim 1, wherein the optoelectronic sensor is a laser scanner.

3. The optoelectronic sensor in accordance with claim 1, wherein the test light transmitter and the test light receiver are not arranged such that they move along with the deflection unit.

4. The optoelectronic sensor in accordance with claim 1, wherein a plurality of test light transmitters and test light receivers are arranged distributed around the deflection unit in a peripheral direction.

5. The optoelectronic sensor in accordance with claim 1, wherein the evaluation unit is configured to acquire a piece of information on the position of the deflection unit from the test light signal.

6. The optoelectronic sensor in accordance with claim 1, wherein the test light reflector has retro-reflecting properties.

7. The optoelectronic sensor in accordance with claim 1, wherein the test light reflector has a plurality of part reflectors which are arranged above one another and/or which are tilted with respect to one another.

8. The optoelectronic sensor in accordance with claim 1, wherein the front screen has the shape of a rotational body and has an inwardly facing contour in a section thereof with respect to a central axis of the rotational body and wherein the test light transmitter and the test light receiver are arranged in a region of the front screen where said front screen has a small radius.

9. The optoelectronic sensor in accordance with claim 1, wherein the front screen has a peripheral base.

10. The optoelectronic sensor in accordance with claim 1, wherein the light transmitter and the light receiver are arranged next to one another in a biaxial design with mutually parallel optical axes.

11. The optoelectronic sensor in accordance with claim 1, wherein a reception lens is arranged upstream of the light receiver and has a close range zone which is significantly larger than a masking by a normed cover object.

12. The optoelectronic sensor in accordance with claim 1, which is configured as a safety light scanner, wherein the evaluation unit is configured to compare the position of detected objects with protected fields and to control a safe output using a shut-down signal on recognizing an unallowed intrusion into a protected field.

13. A method for the transmission monitoring of a front screen of an optoelectronic sensor using a movable deflection unit for a periodic sampling by a light beam, wherein test light is transmitted on at least one test light path through the front screen from a test light transmitter, the test light is reflected at a test light reflector and the reflected test light is converted into a test light signal in a test light receiver and wherein an impaired light permeability of the front screen is recognized from the test light signal, wherein the test light reflector moves along with the deflection unit.

14. The method in accordance with claim 13, wherein the optoelectronic sensor is a laser scanner.

* * * * *